United States Patent
McGee et al.

[11] Patent Number: 5,179,346
[45] Date of Patent: Jan. 12, 1993

[54] CONDUCTIVE PARTICLE SENSOR USING A MAGNET

[75] Inventors: Brian G. McGee, Iowa City, Iowa; Noel J. Rytter, Peoria, Ill.

[73] Assignee: Caterpillar, Inc., Peoria, Ill.

[21] Appl. No.: 705,457

[22] Filed: May 24, 1991

[51] Int. Cl.$^5$ .................. G01R 27/02; G01R 33/12
[52] U.S. Cl. .................. 324/693; 324/204; 340/631
[58] Field of Search .......... 324/693, 204, 219, 228; 340/631, 627; 335/305; 204/61.09; 73/10

[56] References Cited

U.S. PATENT DOCUMENTS

| | | | |
|---|---|---|---|
| 2,429,920 | 10/1947 | Bourne, Jr. | 340/631 |
| 2,462,715 | 9/1949 | Booth | 177/311 |
| 3,373,352 | 3/1968 | Huigens | 324/41 |
| 3,404,337 | 10/1968 | Pool et al. | 324/631 |
| 4,008,464 | 2/1977 | Hobbie | 340/239 |
| 4,100,491 | 7/1978 | Newman et al. | 324/204 |
| 4,219,805 | 8/1980 | Magee et al. | 340/631 |
| 4,323,843 | 4/1982 | Batham | 324/204 |
| 4,686,469 | 8/1987 | Lewis | 340/631 |
| 4,823,625 | 4/1989 | Hamilton | 340/631 |
| 4,831,362 | 5/1989 | Tsaprazis | 340/631 |
| 5,027,065 | 6/1991 | Bares et al. | 324/204 |

FOREIGN PATENT DOCUMENTS

| | | | |
|---|---|---|---|
| 506313 | 5/1939 | United Kingdom | 340/631 |
| 2029580 | 3/1980 | United Kingdom | 324/204 |

OTHER PUBLICATIONS

Komatsu Dresser Company, "Metalert Warning System", Brochure Form No. AK1918.

Primary Examiner—Jack B. Harvey
Assistant Examiner—Maura K. Regan
Attorney, Agent, or Firm—James R. Yee

[57] ABSTRACT

An apparatus is adapted to detect particles within a fluid. The apparatus includes first and second electrodes within a housing. The first and second electrodes form a "V" shaped recess. A magnet is positioned within the housing to attract ferrous particles into the recess. The resistance between the first and second electrodes is measured as an indication of particles within the fluid.

30 Claims, 8 Drawing Sheets

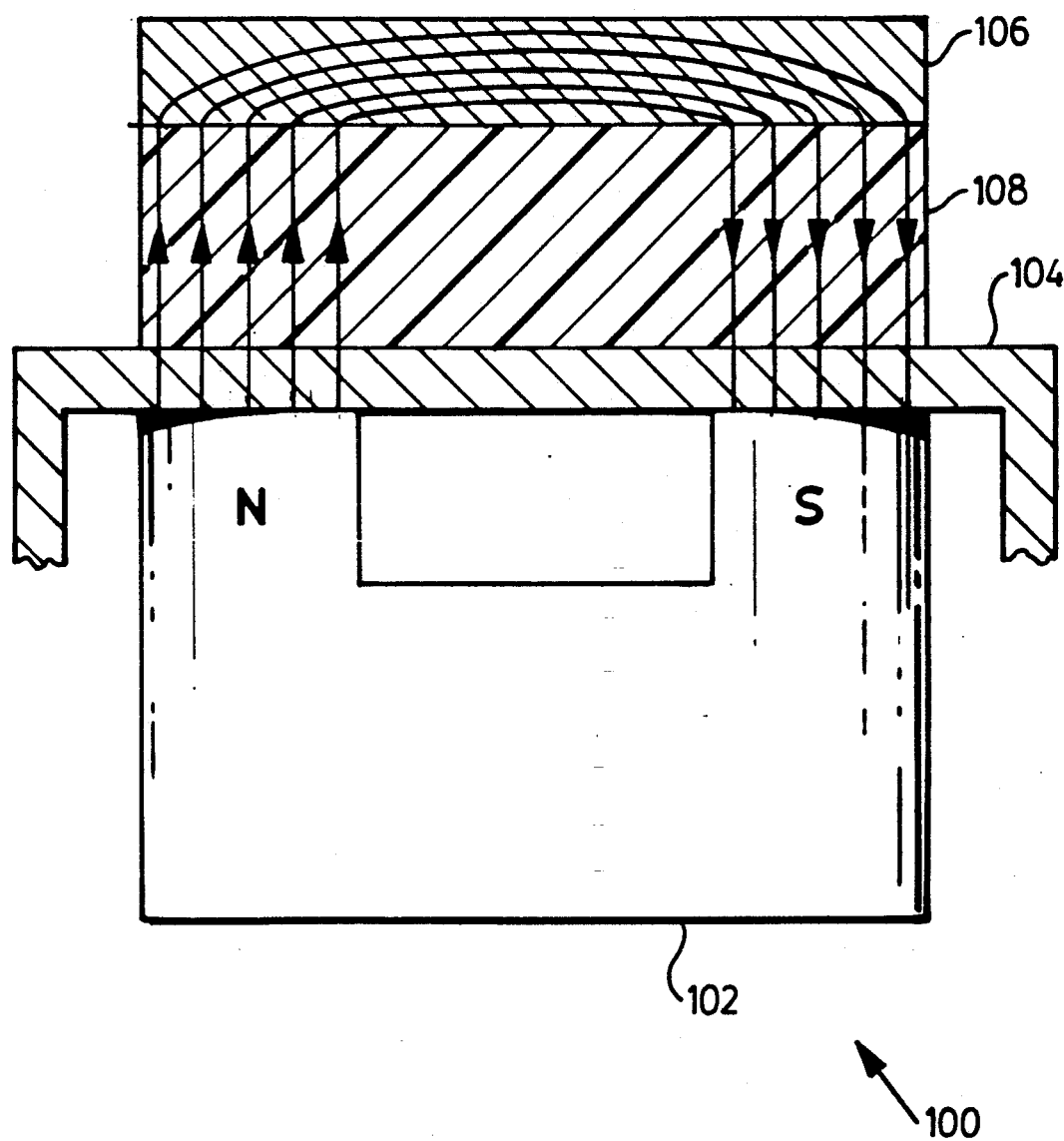
Fig_1_

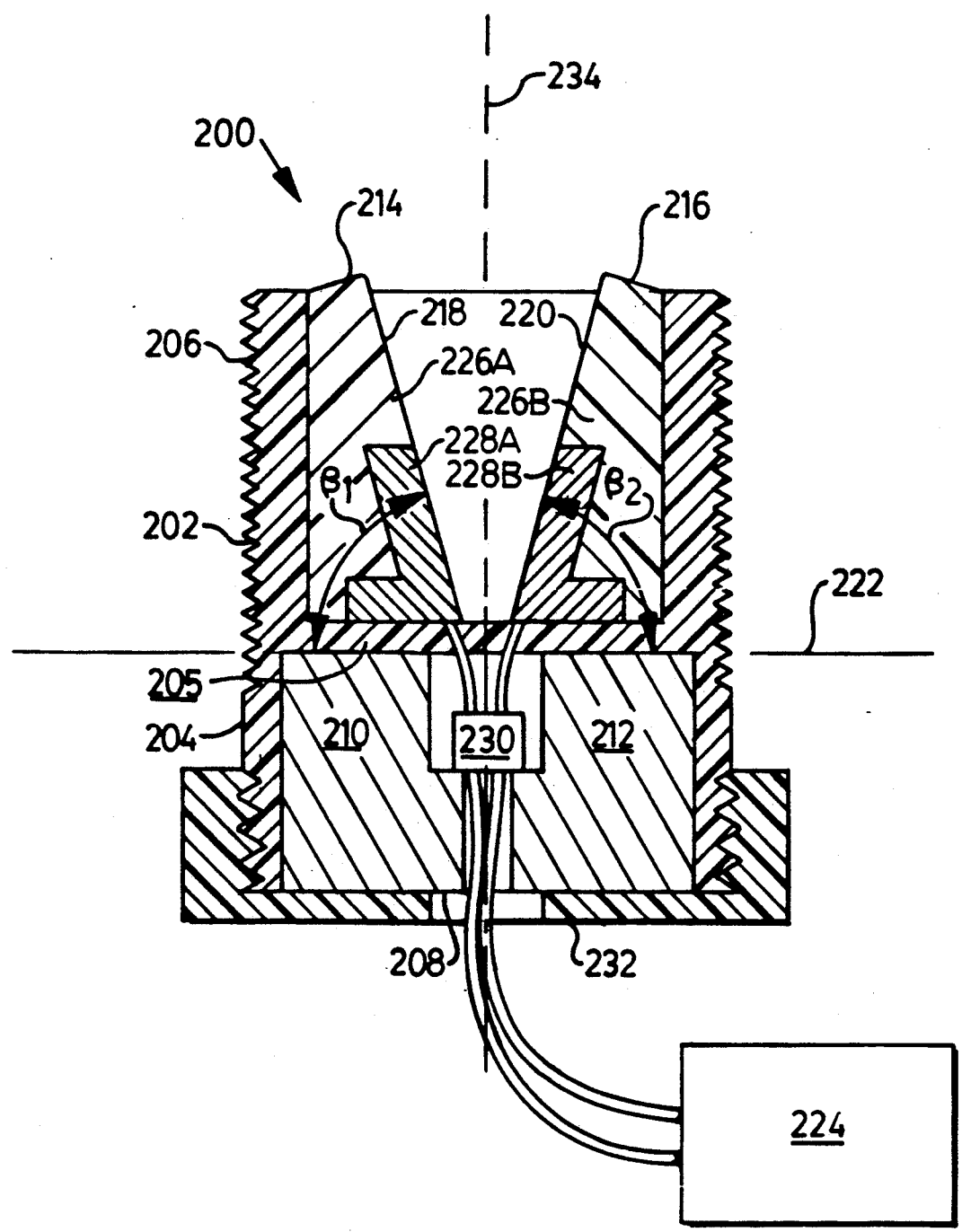
Fig_2a_

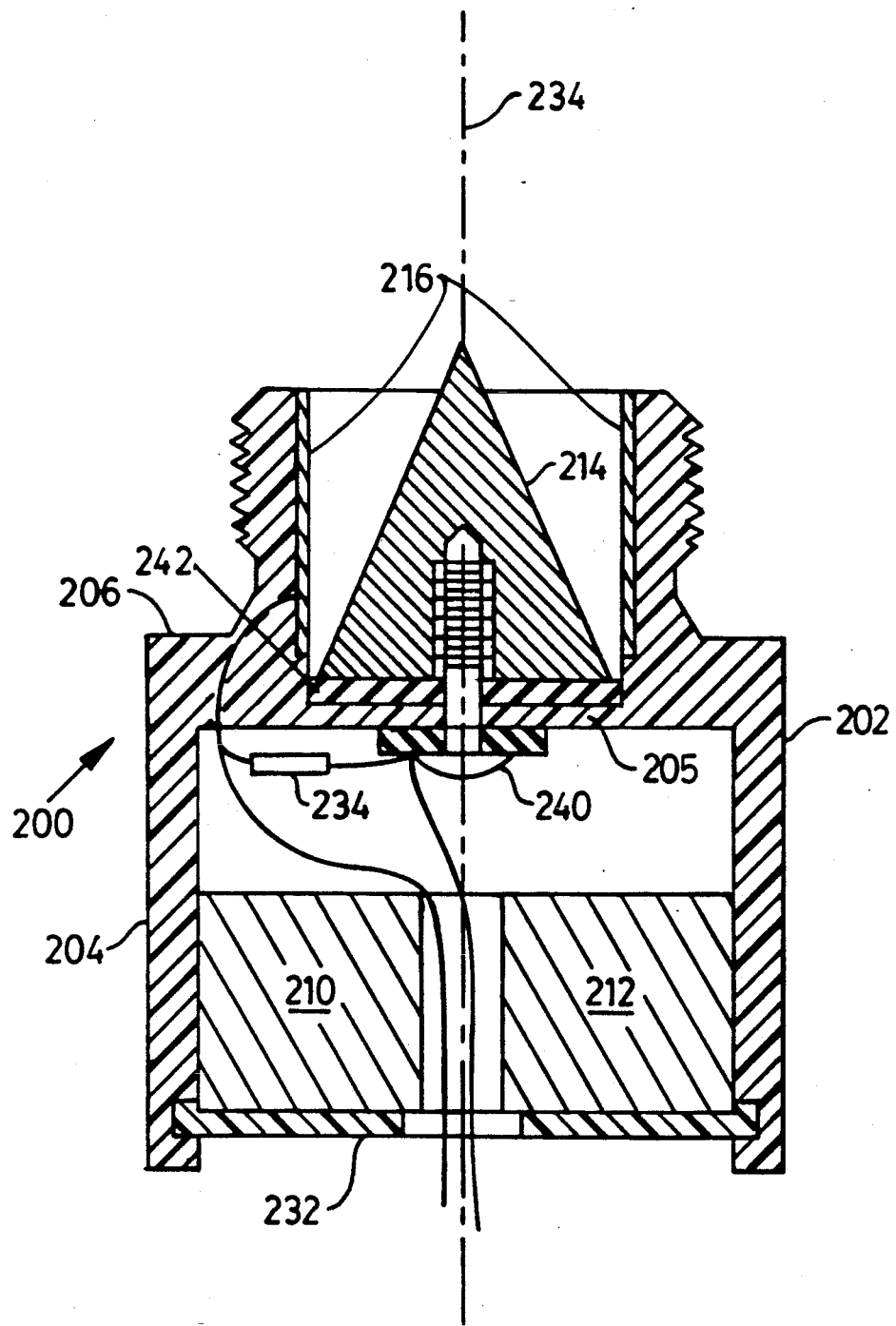
Fig_2b_

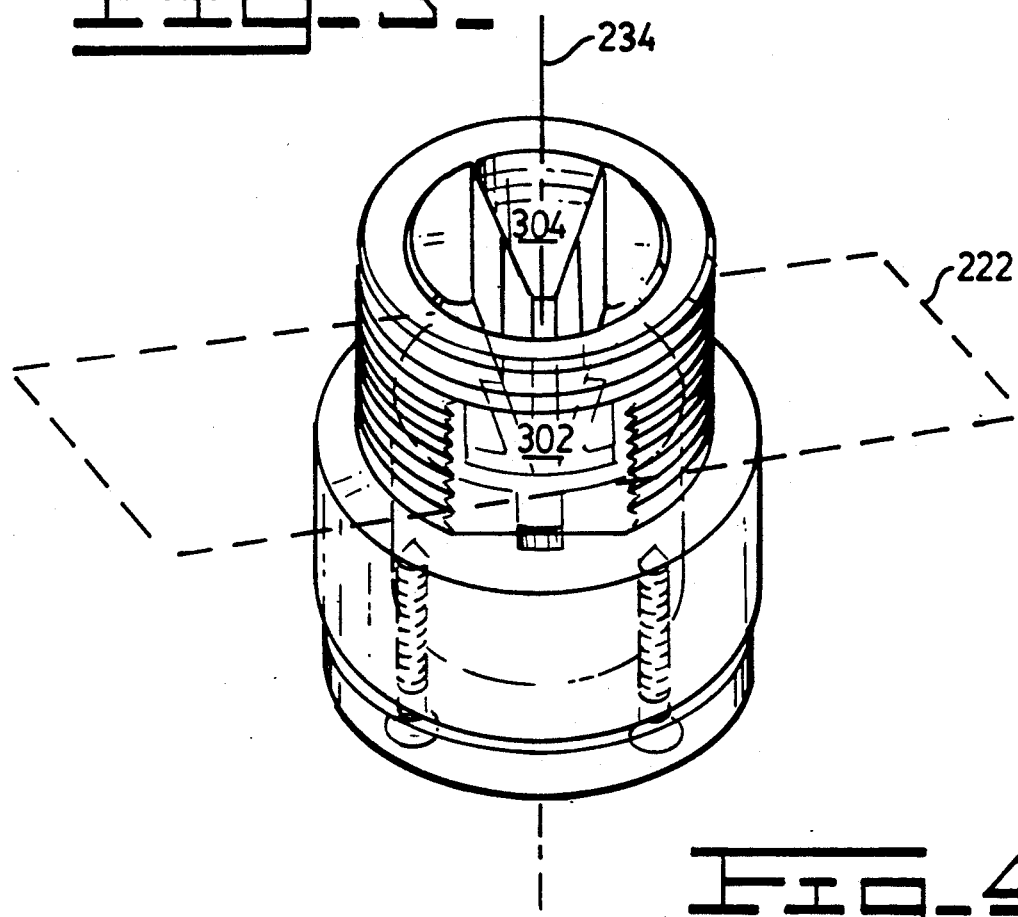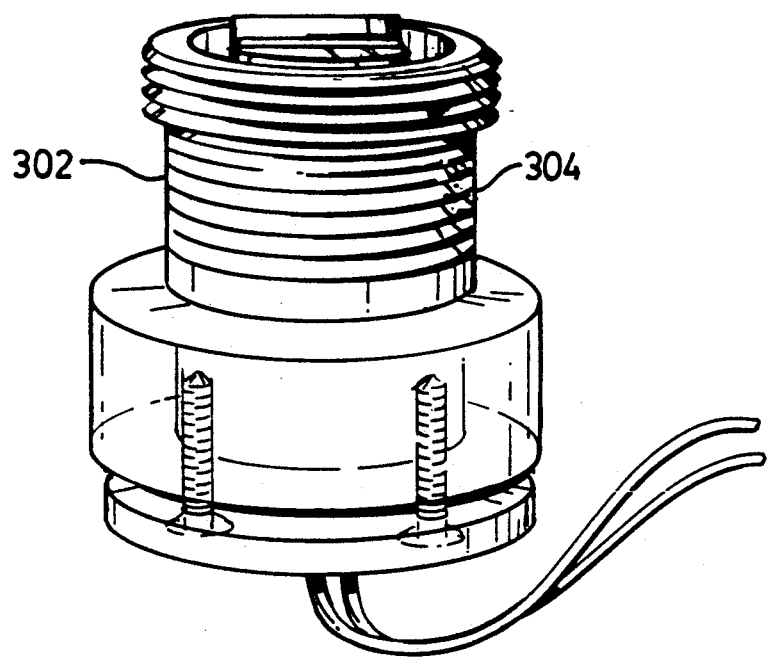

Fig_5_
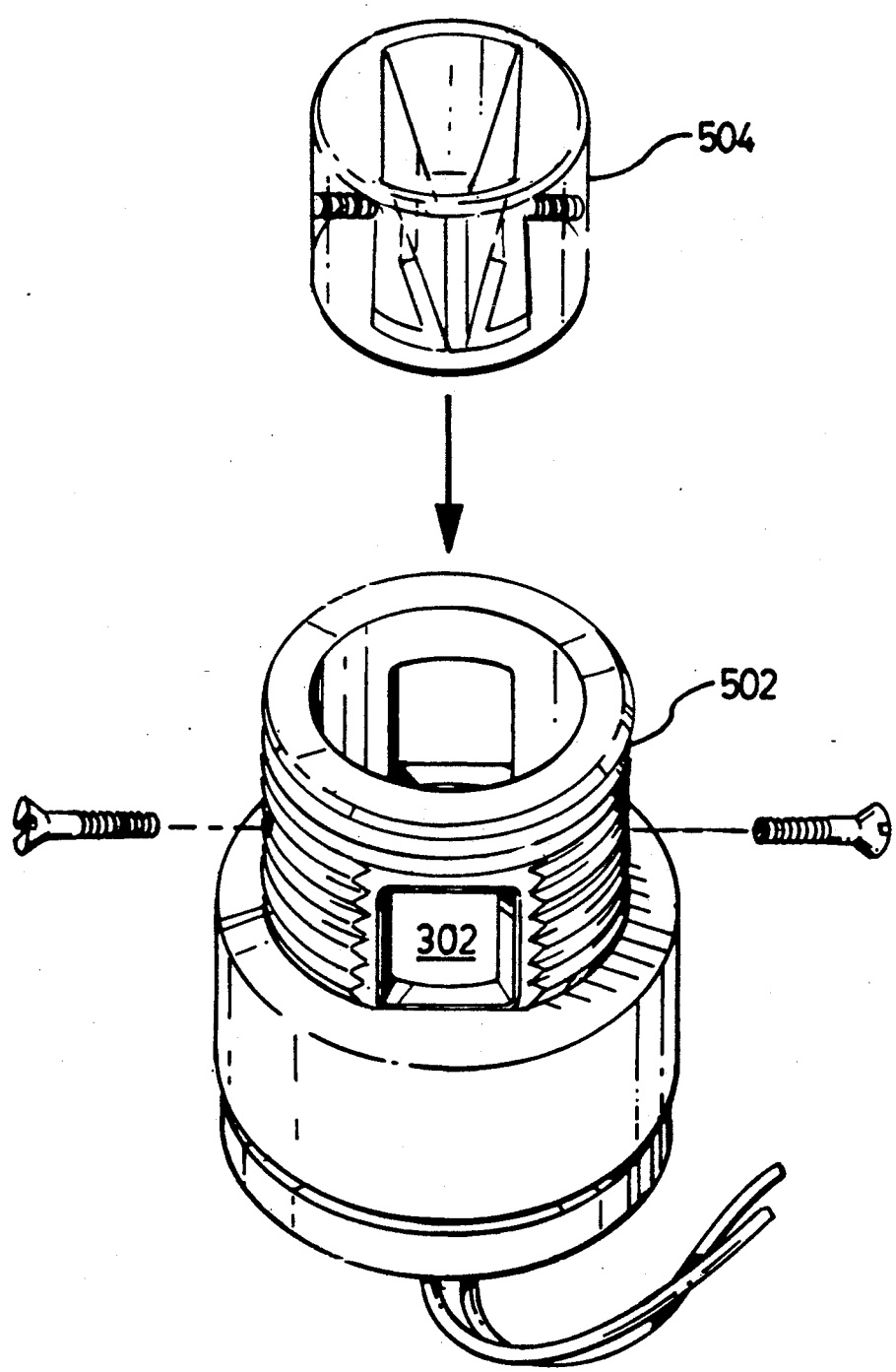

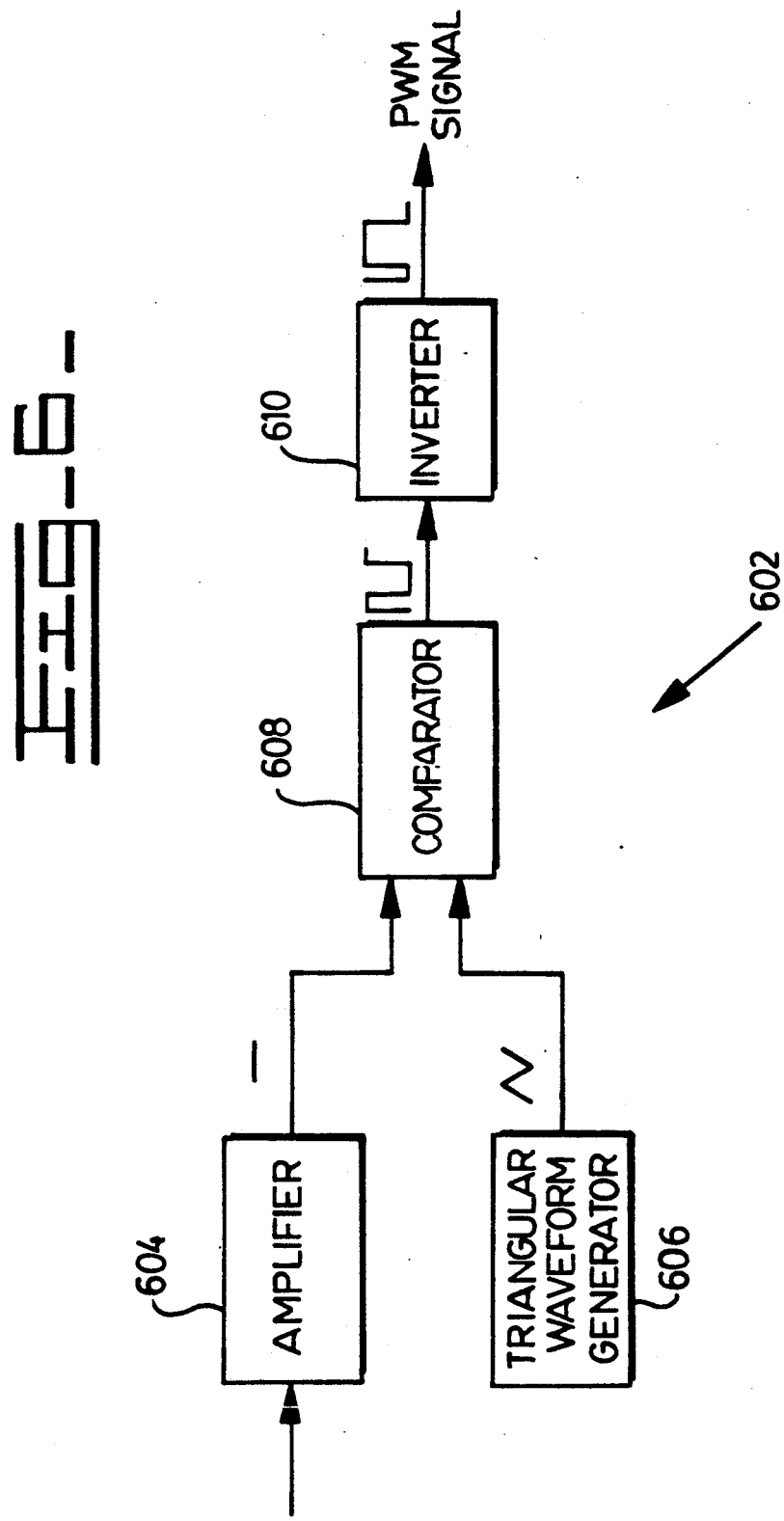

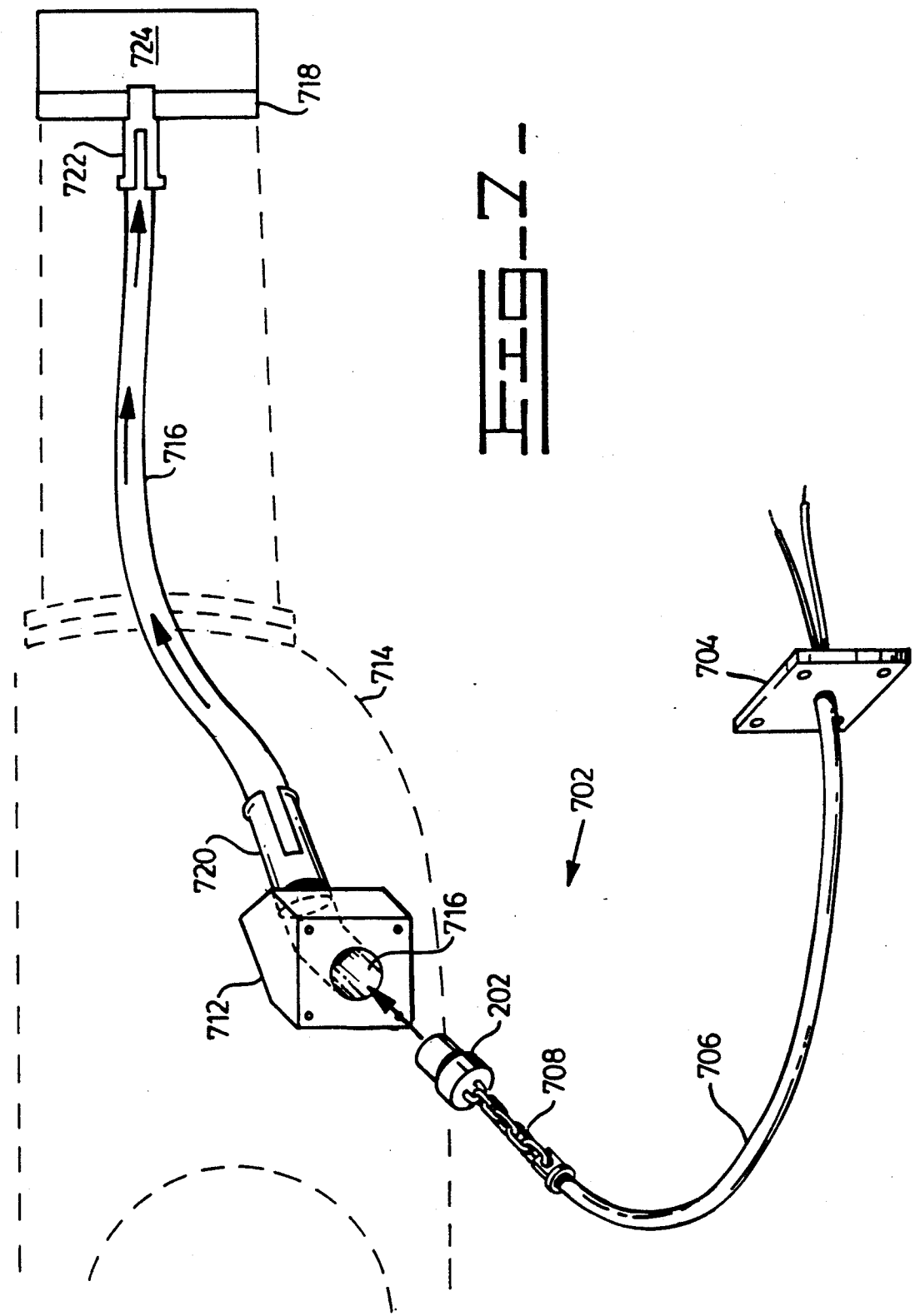

CONDUCTIVE PARTICLE SENSOR USING A MAGNET

DESCRIPTION

TECHNICAL FIELD

This invention relates generally to an apparatus for detecting electrically conductive particles in a fluid medium and more particular for detecting the presence of metal particles in a lubricant.

BACKGROUND ART

Mechanical systems (engines, transmissions) utilize a lubricant (oil) to dissipate heat within the system and to reduce wear on system components. However, due to the nature of the systems, wear does occur, resulting in the presence of metallic flakes or particles in the oil.

Due to the normal wear and to the natural breakdown of the oil, the oil in such systems must be changed periodically. This is typically done on a time or usage basis, for example, every 90 days or 2000 hours of use. The metal particles may be a result of this normal wear, but may also be an indication of abnormal wear or a more serious problem. For example, if the gears within a transmission are not meshing properly, the resulting wear creates abnormal amounts of metal particles within the lubricant. Under normal maintenance procedures, the metal particles would be present in the lubricant for an extended period of time. If this condition is not identified and the appropriate repairs completed, more expensive repairs, including the replacement of major system components, may result.

U.S. Pat. No. 4,323,843 issued Apr. 6, 1982 to Ian N. Batham discloses an apparatus for detecting ferrous contamination in a fluid. A similar device is available from the Komatsu Dresser Company of Peoria, IL under the name Metalert. As shown in, FIG. 1, the apparatus 100 of Batham includes a magnet 102 having north (N) and south (S) poles and first and second electrodes 104,106. The electrodes 104,106 are parallel to the plane formed by the magnet poles, N,S. A spacer 108 electrically isolates the two electrodes 104,106 from each other.

In operation, the electrodes 104,106 and the spacer 108 form a plug which is inserted into a container containing fluid. Ferrous particles are attracted into contact with the two electrodes 104,106 by the magnetic field generated by the magnet 102. The resistance between the two electrodes is measured as an indication of the particles.

There are however several inherent problems with the Batham design. For instance, the sensor design does not protect the particles already attracted to the sensor from currents within the oil. Therefore, particles are continually being "swept" away by the currents. The result is a "noisy" or unstable sensor output. Furthermore, the sensor design does not allow for detecting non-ferrous electrically conductive particles. In some systems, certain system components consist of nonferrous metals, for example, aluminum, brass or bronze. Since the Batham design relies solely on the magnet to attract particles, these types of harmful particles would not be detected.

Furthermore, magnetic particles are more strongly attracted to the top surface of the bottom electrode 104 because it is closer to the magnet. In order for the resistance across the electrodes to change, the particles must "pile up" in order to bridge the gap.

U.S. Pat. No. 2,462,715, issued Sep. 16 1944 to James C. Booth discloses a sensor having two magnetic members connected to a plug. The magnetic members face each other and extend away from the plug into the fluid. This arrangement also has several limitations. First, as in the Batham design, the particles trapped within the sensor may be "swept" away by currents within the fluid. Secondly, since particles are in direct contact with the magnetic members, the particles are not so easily removed for cleaning when the oil is changed.

The present invention is directed to overcoming one or more of the problems, as set forth above.

DISCLOSURE OF THE INVENTION

In one aspect of the invention an apparatus for sensing the presence of electrically conductive particles within a fluid is provided. The apparatus includes a housing and a magnet. The magnet is positioned within a first portion of the housing. A first electrode has a first contact surface and is positioned within the second portion of the housing and extends in a direction generally away from the magnet. A second electrode has a second contact surface and is positioned within the second portion of the housing and extends in a direction generally away from the magnet. The first and second contact surfaces are spaced apart. The apparatus senses the electrical resistance between the first and second contact electrodes and produces a signal indicative of the presence of electrically conductive particles.

BRIEF DESCRIPTION OF THE DRAWINGS

FIG. 1 is a diagrammatic view of a particle sensor as known in the prior art;

FIG. 2A is a cutaway view of a particle sensor, according to one embodiment of the present invention;

FIG. 2B is a cutaway view of a particle sensor, according to another embodiment of the present invention;

FIG. 3 is a diagrammatic view of a particle sensor, illustrating the shape and outside characteristics and the side view ports of the sensor, according to an embodiment of the present invention;

FIG. 4 is another diagrammatic view of a particle sensor, illustrating the shape and outside characteristics and the side view ports of the sensor, according to an embodiment of the present invention;

FIG. 5 is a diagrammatic view of the housing of a particle sensor having an outer shell and an inner shell, according to an embodiment of the present invention;

FIG. 6 is a block diagram of a sensor electronic circuit according to an embodiment of the present invention;

FIG. 7 is a diagrammatic view of a particle sensor mounted on dipstick for long lead applications.

BEST MODE FOR CARRYING OUT THE INVENTION

Figure 8:
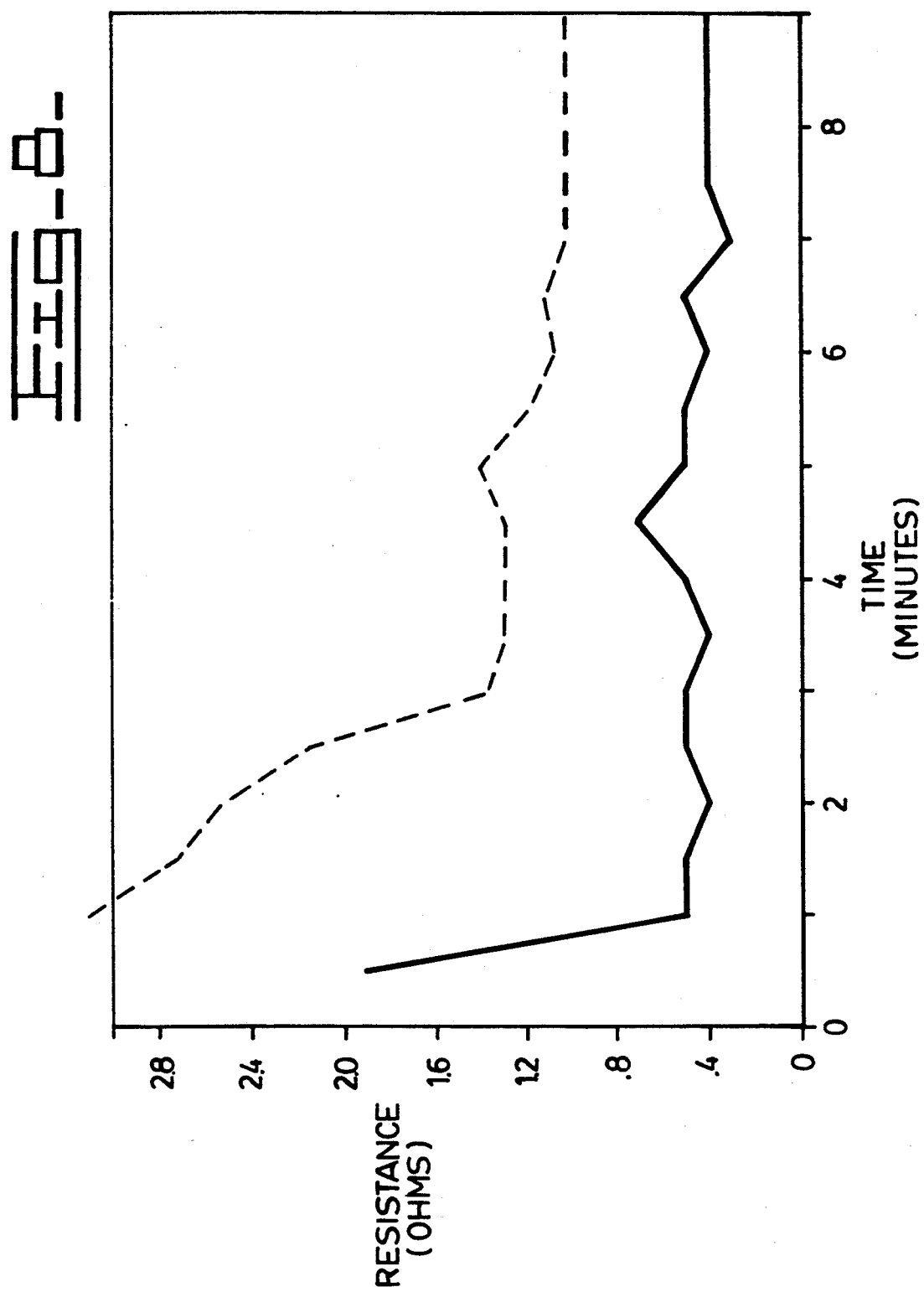
FIG. 8 is a graph of exemplary test runs of a particle sensor according to an embodiment of the present invention.

With reference to FIGS. 2A and 2B, the present invention 200 is adapted to detect particles within the transmission fluid of a transmission (not shown) and is hereafter referred to as apparatus or particle sensor. It should be noted, however, that the use of the present invention for a transmission is for discussion purposes only and is not limited to such. The present invention may be adapted for use in engine oilpans, final drives, differentials, torque converters, hydraulic systems and other similar systems.

The particle sensor 200 includes a housing 202 with first and second portions 204,206. The first and second portions 204,206 are separated by a separation plate 205, which is preferably less than or equal to 0.05 inches thick. The first portion 204 includes a recess. The housing 202 has a generally cylindrical shape centered about an axis 234.

The particle sensor 200 includes a magnet 208. In the preferred embodiment, the magnet 208 is a horseshoe magnet having first and second poles (North and South) 210,212. The magnet 208 is positioned within the recess formed by the first portion 204 of the housing 202. The first and second poles 210,212 define a reference plane 222. The axis 234 is perpendicular to the reference plane 222.

A detachable plate 232 holds the magnet 208 within the recess of the first portion 204 of the housing 202. In one embodiment, the detachable plate 232 and the housing 202 are each threaded, allowing the detachable plate 232 to be fastened to the housing 202. In another embodiment, the detachable plate 232 is fastened to the housing by a set of screws (see FIGS. 3 and 4). In still another embodiment, the plate 232 has wrench flats, that is, bolt shaped, for easy installation of the sensor 200.

First and second electrodes 214,216 are contained within the second portion 206 of the housing 202, forming a cavity.

In a first embodiment, the first electrode 214 includes a first contact surface 218 and is positioned adjacent the first pole 210. The second electrode 216 includes a second contact surface 220 and is positioned adjacent the second pole 212. The first and second electrodes 214,216 extend in directions generally away from the first and second poles 210,212 of the magnet 208, respectfully. The first and second electrodes 214,216 are electrically isolated from the magnet 208 by the separation plate 205 of the housing 202.

The first and second contact surfaces 218,220 are spaced apart and have an angular relationship with the reference plane 222, $\beta_1$, $\beta_2$. In one embodiment, the angular relationship, $\beta_1$, $\beta_2$, between each electrode 218,220 and the reference plane 222 is constant. That is, the angle at one end of the electrode is the same at the opposite end. In a another embodiment, the angular relationship varies along the length of each electrode.

In one embodiment, the electrodes 214,216 are composed of a ferrous, electrically conductive material, for example, steel. Ferrous electrodes under the influence of the permanent magnet 208 become magnets themselves. Ferrous particles are therefore attracted to the electrodes 214,216.

In another embodiment, each electrode includes a guide portion 226A,226B and an insert portion 228A,228B. The guide portions 226A,226B are composed of an electrically conductive material and the insert portions 228A,228B are composed of a ferrous, electrically conductive material, for example, brass and steel, respectively. The ferrous insert portions 228A,228B, as above, become magnets under the influence of the permanent magnet. With this arrangement ferrous particles are attracted to the insert portions 228A,228B. In this manner, small particles are trapped at the bottom of the recess, leaving room for larger particles at the top. The gap between the electrodes 214,216 is smaller at the bottom. Smaller particles are attracted towards the bottom and an immediate change in resistance occurs.

In one embodiment, the housing 202 is composed of a nonconducting and substantially transparent material. One such suitable material is the thermoplastic, Polyethersulfone (PES). For additional strength, the PES may contain glass fibers. Typically, glass-filled PES is 10-40% glass.

With reference to FIG. 3, the housing is threaded about at least a portion of the outside diameter of the housing 202.

First and second unthreaded surfaces 302,304 are positioned opposite each other. In the preferred embodiment, the first and second unthreaded surfaces are substantially flat and parallel.

In still another embodiment, the housing 202 includes an outer shell 502 and an inner shell 504, as shown in FIG. 5. The outer shell 502 is composed of a suitable metal, for example brass. The inner shell 504 is cup-shaped and fits into the outer shell 502. A suitable material for the inner shell 504 is PES. The unthreaded portions 302,304 are machined, preferably oblong shaped, holes in the outer shell 502 of the housing 202.

In a second embodiment, the first electrode 214 is cone-shaped, as shown in FIG. 2B. The second portion 206 forms a circular recess. The second electrode 216 is also circular and surrounds the first electrode 214. A screw 240 holds the first electrode 214 to the housing 202. An insulated washer 242 electrically isolates the first and second electrodes 214,216.

In one embodiment, the housing 202 is composed of a nonconducting material. The second electrode 216 is cupshaped and fits into the second portion of the housing 202.

In another embodiment, the housing 202 is composed of a electrically conducting material. The inner walls of the housing 202 compose the second electrode 216.

A means 224 senses the electrical resistance between the first and second contact electrodes 214,216 and responsively produces a signal indicative of the presence of electrically conductive particles. In the preferred embodiment, the sensing means 224 includes a resistor 230 connected between the first and second electrodes 214,216. The sensing means 224 measures the resistance between the first and second contact electrodes 214,216. If there are no particles within the cavity formed by the first and second electrodes 214,216, the electrodes are effectively an open circuit and only the resistance (1,000 ohms) of the resistor 230 is measured.

This also provides self diagnostic capability. If the resistance between the electrodes 214,216 is greater than 1000 ohms, the sensor 200 is known to be malfunctioning due to a broken wire or loose connection.

In one embodiment, the means 224 includes an ohmmeter (not shown). The ohmmeter may be either an analog or digital device. The output of the ohmmeter may show the magnitude of the measured resistance or include an indicator light that signals an operator when a certain threshold has been passed.

In another embodiment, the means 224 includes a printer or plotter for providing paper or "hardcopy" results. The results may be in the form of graphs, illustrating resistance over time or a series of numbers representing the measured resistance.

In still another embodiment, the sensing means 224 includes means 602 for producing a pulse width modulated (PWM) signal (see FIG. 6). The PWM producing means 602 includes an amplifier 604 for measuring the resistance between the first and second electrodes 214,216 and providing a scaled and filtered signal indicative of the measured resistance. A sawtooth or triangular waveform generator provides a reference signal against which the output of the amplifier is compared by a comparator 608. The output of the comparator 608 is a pulse width modulated signal. The width of the pulse is proportional to the measured resistance. An inverter 610 inverts the output of the comparator 608 and isolates the output from the PWM signal producing means 602. The pulse width of the output of the inverter 610 is inversely proportional to the measured resistance and is provided to an electronic control module (ECM), not shown. The ECM is, typically, microprocessor based and is adapted to receive the PWM signal. The ECM is capable of measuring the length of each pulse which is then translated into a signal representing particles within the lubricating fluid. Such a sensor to ECM arrangement is well known in the art and is therefore not further discussed.

In some applications, placement of the particle sensor 202 in a suitable position is adversely affected by the oil container, for example, a final drive cavity. One solution to this problem is a dipstick assembly 702, as shown in FIG. 7. The dipstick assembly 702 includes a dipstick cap 704, a flexible dipstick 706, and a flexible joint 708. A piece of hydraulic hose has been found to be suitable for use as a dipstick. The cap 232 of the particle sensor 202 is connected at the end of the flexible joint 708, as shown. The flexible joint 708 may be a piece of chain or a ball and socket arrangement.

One advantage of this arrangement is that the dipstick assembly 702 can be inserted through the oil fill access hole 710 of the differential housing 714. An access port manifold 712 is mounted to the differential housing 714 (shown in dotted lines). The dipstick assembly 702 is inserted into the access port manifold 712 and passes through a second tube or piece of hydraulic hose 716 with a larger diameter. The second piece of hydraulic hose 716 is connected to the access port manifold and to a reaction plate 718 by first and second hose clamps 720,722. The dipstick assembly 702 is inserted such that the particle sensor 202 passes through the second hose clamp 722 and is in position to collect particles from the final drive cavity 724.

The dipstick arrangement also allows the sensor 200 to be inspected without disassembly of the final drive.

Tests have shown that not only is the measured resistance indicative of the presence or absence of particles, the magnitude of the measured resistance is indicative of the size of the particles trapped within the particle sensor 200. FIG. 8 illustrates the results of these tests in which a particle sensor was inserted at the bottom of a container filled with four (4) liters of #30 weight engine oil. In one series of tests, small iron particles, 2-3 cubic mm in volume were placed in the oil, the oil was agitated, and particles allowed to collect in the sensor 200. The graph of FIG. 8 shows only the resistance of the electrodes and the particles, that is the resistor 230 was not used.

Typical results of this series of tests are illustrated in the dotted line of FIG. 8. The dotted line illustrates a few important operating characteristics of the particle sensor 200. As more and more particles become present within the oil, the resistance measured between the first and second electrodes decreases. Second, the resistance reaches an equilibrium resistance.

In a second series of tests, larger steel particles, approximately 3-5 cubic mm in volume, were introduced into the oil.

The results of this series of tests are exemplified by the solid line in FIG. 8. While the solid line illustrates that the resistance decreases and reaches an equilibrium resistance as above, it also shows that the equilibrium resistance is lower for the larger particles than for smaller particles. This is attributed to the fact that the particles are "floating" within the oil. The resistance path consists of the particles and the "gaps" between the particles which are filled with oil. Since the gaps have a larger electrical resistance than the particles and there are less gaps in the resistance path, there exists a lower overall resistance between the first and second electrodes 214,216.

Furthermore, the two lines illustrate another important characteristic of the sensor 200: the rate of decrease in resistance is larger for larger particles. Therefore, the slope of the resistance curve also indicates the relative size of the particles collected by the sensor 200.

INDUSTRIAL APPLICABILITY

With reference to the drawings and in operation, the present invention is adapted to sense the presence of particles in the transmission fluid of a vehicles transmission.

In the preferred embodiment, the particle sensor 200 is positioned in an upright position within the transmission. The particle sensor 200 is screwed into a plate of the transmission by the threads around the outside diameter. The first and second electrodes 214,216 include guide portions 226A,226B and insert portions 228A,228B, as discussed above.

This two piece electrode arrangement and the v-shaped recess formed by the first and second electrodes 214,216 allow a large size range of particles to be detected by the sensor 200 while maintain the sensitivity of the sensor 200 to smaller particles. Smaller particles will be attracted towards the bottom of the recess, while larger particles will remain towards the top because of their size.

Additionally, the v-shaped arrangement shields the collected particles from oil currents.

Furthermore, this arrangement also allows nonferrous particles to contribute to the resistance measured between the first and second electrode 214,216. Nonferrous particles, while not being attracted by the magnet, will naturally collect in the recess formed by the electrodes 214,216. This is especially important in systems in which components are made of nonferrous electrically conductive materials.

During operation of the vehicle, the transmission fluid may be changed according to regular maintenance procedures. Optionally or in combination, the particle sensor 200 may also be used as an indication that the fluid is in need of replacement due to normal wear and abnormal wear.

The unthreaded surfaces 302,304 may also be utilized to indicate the state of the oil. By partly unscrewing the particle sensor 200, the particles trapped within the sensor 200 may be seen through the surfaces. This may be done without the need for draining the transmission or without losing any oil.

As discussed above, the particle sensor 200, may be connected to an indicator, which signals to an operator when the measured resistance is below a threshold. The measured resistance and/or change in resistance may also be used as an indication of the size and/or type of particles present in the fluid, as discussed above.

When the transmission fluid is changed, it may also be necessary to clean the sensor. This is easily done by removing the sensor from the transmission, detaching the plate 232 and removing the magnet 208. The particles in the sensor 200 can than be removed easily.

Other aspects, objects, and advantages of the present invention can be obtained from a study of the drawings, the disclosure, and the appended claims.

We claim:

1. An apparatus for sensing electrically conductive particles within a fluid, comprising:
   a housing having first and second portions;
   a magnet having a first pole and a second pole and being positioned within said first portion of said housing, said first and second poles defining a reference plane;
   a first electrode having a first contact surface and being positioned within said second portion of said housing and extending in a direction generally away from said magnet;
   a second electrode having a second contact surface and being positioned within said second portion of said housing and extending in a direction generally away from said magnet, said first and second contact surfaces being spaced apart and each having an angular relationship with said reference plane; and
   means for sensing the electrical resistance between said first and second contact electrodes and responsively producing a signal indicative of the presence of said electrically conductive particles.

2. An apparatus, as set forth in claim 1, wherein the said first and second contact surfaces form a v-shaped cavity.

3. An apparatus, as set forth in claim 1, wherein the magnitude of said signal is indicative of the amount of particles within said fluid.

4. An apparatus, as set forth in claim 1, wherein the magnitude of said signal is indicative of the size of the particles within said fluid.

5. An apparatus, as set forth in claim 1, wherein said first and second electrodes are composed of steel.

6. An apparatus, as set forth in claim 1, wherein said first and second electrodes are composed of a ferrous and electrically conductive material.

7. An apparatus, as set forth in claim 1, wherein said means for responsively producing a signal indicative of the presence of said electrically conductive particles includes means for producing a pulse width modulated signal having a duty cycle inversely proportional with said electrical resistance.

8. An apparatus, as set forth in claim 1, wherein said housing is composed of a substantially transparent material.

9. An apparatus, as set forth in claim 8, wherein said housing has a generally cylindrical shape centered about an axis perpendicular to said reference plane.

10. An apparatus, as set forth in claim 9, wherein said housing is threaded about at least a portion of the outside diameter of said housing.

11. An apparatus, as set forth in claim 10, wherein said housing includes first and second unthreaded surfaces positioned opposite each other, said first and second unthreaded surfaces being substantially flat and substantially perpendicular to said first and second electrodes.

12. An apparatus, as set forth in claim 1, wherein said housing is composed of a polyethersulfone.

13. An apparatus, as set forth in claim 1, wherein said housing is composed of a polyethersulfone reinforced with glass fibers.

14. An apparatus, as set forth in claim 1, wherein said housing includes an inner shell and an outer shell.

15. An apparatus, as set forth in claim 14, wherein said inner shell is composed of a substantially transparent material.

16. An apparatus, as set forth in claim 1, wherein said housing has a generally cylindrical shape centered about an axis perpendicular to said reference plane.

17. An apparatus, as set forth in claim 16, wherein said housing is threaded about at least a portion of the outside diameter of said housing.

18. An apparatus for sensing electrically conductive particles within a fluid, comprising:
   a housing first and second portions;
   a magnet having a first pole and a second pole and being positioned with said first portion of said housing, said first and second poles defining a reference frame;
   a first electrode having a first contact surface and being positioned within said second portion of said housing and extending in a direction generally away from said magnet;
   a second electrode having a second contact surface and being positioned within said second portion of said housing and extending in a direction generally away from said magnet, said fist and second contact surfaces being spaced apart and each having an angular relationship with said reference frame, wherein said first and second electrodes each include a guide portion and an insert portion; and,
   means for sensing the electrical resistance between said fist and second contact electrodes and responsively producing a signal indicative of the presence of said electrically conductive particles.

19. An apparatus, as set forth in claim 18, wherein said insert portions are composed of a ferrous and electrically conductive material and said guide portions are composed of an electrically conductive material.

20. An apparatus, as set forth in claim 18, wherein said insert portions are composed of steel and said guide portions are composed of brass.

21. An apparatus for sensing electrically conductive particles within a fluid, comprising:
   a housing having first and second portions;
   a magnet having a first pole and a second pole and being positioned with said first portion of said housing, said first and second poles defining a reference frame;
   a first electrode having a first contact surface and being positioned within said second portion of said housing and extending in a direction generally away from said magnet;
   a second electrode having a second contact surface and being positioned within said second portion of said housing and extending in a direction generally away from said magnet, said first and second contact surfaces being spaced apart and each having an angular relationship with said refer e frame, wherein said fist and second contact surfaces have a length extending along said fist and second poles, respectively, said angular relationship varying along said length; and, means for sensing the electrical resistance between said first and second contact electrodes and responsively producing a signal indicative of the presence of said electrically conductive particles.

22. An apparatus, as set forth in claim 21, wherein said inner shell is composed of a polyethersulfone.

23. An apparatus, as set forth in claim 22, wherein said polyethersulfone is reinforced with glass fibers.

24. An apparatus for sensing electrically conductive particles within a fluid, comprising:

a housing having first and second portions;

a magnet having a first pole and a second pole and being positioned with said first portion of said housing, said fist and second poles defining a reference frame;

a first electrode having a first contact surface and being positioned within said second portion of said housing and extending in a direction generally away from said magnet;

a second electrode having a second contact surface and being positioned within said second portion of said housing and extending in a direction generally away from said magnet, said first and second contact surfaces being spaced apart and each having an angular relationship with said reference frame; and, means for sensing the electrical resistance between said fist and second contact electrodes and responsively producing a signal indicative of the presence of said electrically conductive particles, wherein said sensing means includes:

a resistor having first and second terminals, said first and second terminals being connected to said fist and second electrodes, and means for measuring the electrical resistance across said first and second terminals.

25. An apparatus for sensing electrically conductive particles within a fluid, comprising:

a housing first and second portions;

a magnet having a first pole and a second pole and being positioned with said first portion of said housing, said first and second poles defining a reference frame;

a first electrode having a first contact surface and being positioned within said second portion of said housing and extending in a direction generally away from said magnet;

a second electrode having a second contact surface and being positioned within said second portion of said housing and extending in a direction generally away from said magnet, said first and second contact surfaces being spaced apart and each having an angular relationship with said reference frame; and, mean of sensing the electrical resistance between said first and second contact electrodes and responsively producing a signal indicative of the presence of said electrically conductive particles, wherein said housing includes a recess for said magnet and including a detachable plate adapted to hold said magnet within the recess of said housing.

26. An apparatus for sensing the presence of electrically conductive particles within a fluid, comprising:

a housing having first and second portions, said housing having a generally cylindrical shape centered about an axis and being composed of a substantially transparent material;

a magnet having a first pole and a second pole and being positioned within a recess of said first portion of said housing, said first and second poles defining a reference plane, said axis being perpendicular to said reference plane;

a detachable plate adapted to hold said magnet within the recess of said housing;

a first electrode having a first contact surface and being positioned within said second portion of said housing;

a second electrode having a second contact surface and being positioned within said second portion of said housing, said fist and second contact surfaces being spaced apart;

wherein said hosing is threaded about at least a portion of the outside diameter of said housing and includes first and second unthreaded surfaces positioned opposite each other and substantially perpendicular to said first and second electrodes; and means for sensing the electrical resistance between said first and second contact electrodes and responsively producing a signal indicative to the presence of said electrically conductive particles.

27. An apparatus, as set forth in claim 26, wherein said housing is composed of a polyethersulfone.

28. An apparatus, as set forth in claim 26, wherein said housing is composed of a polyethersulfone reinforced with glass fibers.

29. An apparatus for sensing the presence of electrically conductive particles within a fluid, comprising:

a housing having first and second portions, said housing having a generally cylindrical shape centered about an axis and being composed of a substantially transparent material;

a magnet having a first pole and a second pole and being positioned within a recess of said first portion of said housing, said first and second poles defining a reference plane, said axis being perpendicular to said reference plane;

a first electrode having a first contact surface and being positioned adjacent said first pole within said second portion of said housing and extending in a direction generally away from said first pole;

a second electrode having a second contact surface and being positioned adjacent said second pole within said second portion of said housing and extending in a direction generally away from said second pole, said first and second contact surfaces being spaced apart and each having an angular relationship with said reference plane; and a detachable plate adapted to hold said magnet within the recess of said housing;

wherein said housing is threaded about at least a portion of the outside diameter of said housing and includes first and second unthreaded surfaces positioned opposite each other and substantially perpendicular to said first and second electrodes; and means for sensing the electrical resistance between said first and second contact electrodes and responsively producing a signal indicative of the presence of said electrically conductive particles.

30. An apparatus for sensing the presence of electrically conductive particles within a fluid, comprising:

a housing having an inner shell and an outer shell, said housing having a generally cylindrical shape centered about an axis, said inner shell being composed of a substantially transparent material, said housing having first and second portions;

a magnet having a first pole and a second pole and being positioned within a recess of said first portion of said housing, said first and second poles defining a reference plane, said axis being perpendicular to said reference plane;

a first electrode having a first contact surface and being positioned adjacent said first pole within said second portion of said housing and extending in a direction generally away from said first pole;

a second electrode having a second contact surface and being positioned adjacent said second pole within said second portion of said housing and extending in a direction generally away from said second pole, said first and second contact surfaces being spaced apart and each having an angular relationship with said reference plane; and a detachable plate adapted to hold said magnet within the recess of said housing;

wherein said housing is threaded about at least a portion of the outside diameter of said housing and includes first and second unthreaded surfaces positioned opposite each other and substantially perpendicular to said first and second electrodes; and means for sensing the electrical resistance between said first and second contact electrodes and responsively producing a signal indicative of the presence of said electrically conductive particles.

* * * * *

UNITED STATES PATENT AND TRADEMARK OFFICE
CERTIFICATE OF CORRECTION

PATENT NO. : 5,179,346

DATED : January 12, 1993

INVENTOR(S) : Brian G. McGee and Noel J. Rytter

It is certified that error appears in the above-identified patent and that said Letters Patent is hereby corrected as shown below:

Column 8, line 23, insert --having-- after "housing".

Column 8, line 35, "fist" should be --first--.

Column 8, line 42, "fist" should be --first--.

Column 8, line 68, "refer e" should be --reference--.

Column 9, line 1, "fist" should be --first--.

Column 9, line 2, "fist" should be --first--.

Column 9, line 18, "fist" should be --first--.

Column 9, line 33, "fist" should be --first--.

Column 9, line 39, "fist" should be --first--.

Column 9, line 44, insert --having-- after "housing".

Column 9, line 60, delete "mean of" and insert --means for--.

Column 10, line 17, "fist" should be --first--.

Signed and Sealed this

Twenty-third Day of November, 1993

Attest:

BRUCE LEHMAN

*Attesting Officer*   *Commissioner of Patents and Trademarks*